United States Patent [19]

Sander

[11] Patent Number: 5,269,783
[45] Date of Patent: Dec. 14, 1993

[54] DEVICE AND METHOD FOR REPAIRING TORN TISSUE

[75] Inventor: Thomas Sander, Newtown Road, Conn.

[73] Assignee: United States Surgical Corporation, Norwalk, Conn.

[21] Appl. No.: 699,991

[22] Filed: May 13, 1991

[51] Int. Cl.$^5$ .................. A61B 17/56; A61B 17/00; A61B 17/06; A61F 2/32

[52] U.S. Cl. .................. 606/72; 606/75; 606/77; 606/88; 606/222; 606/224; 606/228; 606/230; 606/232

[58] Field of Search .................. 606/72, 74, 75, 77, 606/60, 139, 222, 223, 224, 228, 230, 232, 148, 151, 219, 220, 233

[56] References Cited

U.S. PATENT DOCUMENTS

| | | | |
|---|---|---|---|
| 2,075,508 | 3/1937 | Davidson | 606/232 |
| 2,199,025 | 4/1940 | Conn | 606/232 |
| 2,802,468 | 8/1957 | Everett | 606/226 |
| 3,123,077 | 3/1964 | Alcamo | 606/228 |
| 3,570,497 | 3/1971 | Lemole . | |
| 3,875,946 | 4/1975 | Duncan . | |
| 3,890,975 | 6/1975 | McGregor . | |
| 3,976,079 | 8/1976 | Samuels et al. | 606/232 |
| 3,981,307 | 9/1976 | Borysko | 606/224 X |
| 4,344,193 | 8/1982 | Kenny . | |
| 4,359,053 | 11/1982 | Benjamin | 606/226 |
| 4,549,545 | 10/1985 | Levy | 606/223 X |
| 4,635,637 | 1/1987 | Schreiber . | |
| 4,649,920 | 3/1987 | Rhum | 606/230 |
| 4,712,550 | 12/1987 | Sinnett . | |
| 4,741,330 | 5/1988 | Hayhurst . | |
| 4,781,190 | 11/1988 | Lee . | |
| 4,790,303 | 12/1988 | Steffee | 606/72 X |
| 4,858,603 | 8/1989 | Clemow . | |
| 4,869,242 | 9/1989 | Galluzzo . | |
| 4,873,976 | 10/1989 | Schreiber . | |
| 4,875,479 | 10/1989 | Belykh et al. | 606/230 |
| 4,895,148 | 1/1990 | Bays et al. . | |
| 4,901,712 | 2/1990 | Voegell et al. . | |
| 4,926,860 | 5/1990 | Stice et al. . | |
| 4,950,285 | 8/1990 | Wick | 606/151 X |
| 4,976,715 | 12/1990 | Bays et al. . | |
| 4,981,149 | 1/1991 | Yoon et al. | 606/224 X |
| 4,997,436 | 3/1991 | Oberlander . | |
| 5,002,562 | 3/1991 | Oberlander . | |
| 5,035,707 | 7/1991 | Korthoff | 606/227 X |
| 5,053,047 | 10/1991 | Yoon . | |
| 5,059,206 | 10/1991 | Winters . | |
| 5,102,421 | 4/1992 | Anspach, Jr. . | |
| 5,154,189 | 10/1992 | Oberlander . | |

FOREIGN PATENT DOCUMENTS

| | | | |
|---|---|---|---|
| 314412 | 5/1989 | European Pat. Off. | 606/228 |
| 0390613 | 10/1990 | European Pat. Off. . | |
| 8701270 | 3/1987 | PCT Int'l Appl. . | |
| 3396 | 6/1986 | World Int. Prop. O. | 606/224 |

OTHER PUBLICATIONS

Ethicon Brochure, 1966 4 pages.
A brochure entitled "The Meniscal Anchor" from GMI, Inc.
"A Needle Guided Resorbable Staple for Arthoscopic Meniscal Repair" by Daniel F. Justin.
"A Technique of Arthroscopic Meniscoplasty" by Vincent J. DiStefano, MD and Paul Bizzle, DO.
"Arthroscopic Meniscal Repair" by William G. Clancy, Jr., MD and Ben K. Graf, MD.
"Arthroscopic Repair of Meniscus Tears" by Charles E. Henning, MD.

*Primary Examiner*—Michael A. Brown
*Attorney, Agent, or Firm*—Thomas R. Bremer; Peter G. Dilworth; Rocco S. Barrese

[57] ABSTRACT

A device for repairing torn tissue or muscle such as the meniscus of the knee. The device consists of a pair of needles detachably secured to a pair of anchoring members having a plurality of barb-like projections extending outwardly therefrom. The anchoring members are joined by a suture which connects the ends of the anchoring members opposite the needles.

20 Claims, 8 Drawing Sheets

DEVICE AND METHOD FOR REPAIRING TORN TISSUE

BACKGROUND OF THE INVENTION

1. Field Of The Invention

The present invention relates to a device for repairing torn tissue and muscle in the body, and more particularly to a device for repairing a torn meniscus in the human knee. A method of repairing torn meniscal tissue is also disclosed.

2. Discussion Of The Prior Art

The surgical repair of torn tissue and muscles in the body has typically been performed through incisions in the body to expose the area under repair and the actual procedure includes the provision of sutures, staples or fasteners The advent of arthroscopic techniques and endoscopic equipment have reduced the size and depth of the incision required to perform the repair procedure; however, the use of conventional devices in many cases requires a highly skilled surgeon to perform the repair, and usually requires complete immobilization of the surgical area following the repair procedure.

Surgical repair of cartilage and muscle in joints such as the knee often requires extraordinary skill on the part of the surgeon to reduce damage to adjacent nerves, blood vessels, muscles and tendons in the knee joint In particular, surgical repair of the fibrocartilage disks within the knee known as the menisci, which are attached peripherally to the joint capsule, requires precision to avoid such damage.

In the past, meniscal surgery has included procedures for partial to complete removal of a torn meniscus, as well as attempts to surgically suture or staple the tear in the meniscus to allow for healing. Other techniques have included removal of portions of the meniscus to arrest the spread of the tear.

A technique has been developed using arthroscopic instruments which provides for meniscal repair through the use of a pair of surgical needles which are inserted through cannuli into the knee on opposite sides of the tear in the meniscus to be repaired. The needles are linked by a single suture which is pushed down through the cannuli and across the tear. An incision is made in the skin at the point where the needles exit the knee joint so that the leading end of each needle may be grasped and pulled through the joint. The ends of the sutures are then grasped after the needles are removed from the suture ends and the suture is then tied outside the skin so that a horizontal suture is created in the meniscus. This procedure is repeated for placement of as many sutures as necessary to repair the meniscus tear. This process is very time consuming, and the strength of the repair is dependent upon the tension created by the knot tied in the suture.

The need exists for a device for repairing torn tissue, such as the meniscus of the knee, which obviates the disadvantages encountered in the prior art and provides an efficient, suture-type device which expedites the surgical procedure and reduces the amount of precision necessary on the part of the surgeon during the procedure.

SUMMARY OF THE INVENTION

The present invention provides a novel device for repairing torn tissue and muscle such as the menisci in the knee joint which expedites the surgical process and facilitates complete healing of the tear. The device of the present invention reduces the precision required on the part of the surgeon to accurately place and secure the suture at the tear site, and expedites the surgical process by eliminating the requirement of securing the ends of the sutures together to stitch the tear. The device of the present invention allows a surgeon to reduce the trauma to the surrounding tissue and facilitates healing of the torn muscle tissue by providing a completely resorbable suture-like device which may be accurately placed across the tear and which may remain in place until the tear is completely healed.

The device for repairing torn tissue and muscles of the present invention comprises a pair of surgical needles each secured at one end to a pair of anchoring members which essentially comprise absorbable rods having outwardly projecting barbs. Each anchoring member is secured at a second end to an absorbable flexible material such as a suture which extends between the two anchoring members. The means of securement between the needles and anchoring members, and between the anchoring members and the suture may include adhesives, swaging, crimping or a quick-release connection such as heat-shrinkable tubing. Preferably, the suture and the anchoring members are constructed of a bioresorbable material.

The barbs of the anchoring member have a tapered configuration towards the needles so that as the needles are pushed through the tissue, the barbs easily pass through the tissue with the needle. The configuration of the barbs is such that the anchoring members pass easily through the tissue in the forward direction, but are prevented from moving in the reverse direction. The barbs are provided to anchor the device in the tissue.

The needles of the present invention may be straight needles, preferably constructed of stainless steel or other surgical grade metal alloy. Although preferably straight, it is contemplated that the needles may be curved, similar to suture-type needles.

In use, the damaged or torn meniscus in the knee is arthroscopically approached from the front of the knee by inserting the needles across the tear and then advancing the needles through the meniscus across the tear, drawing the absorbable anchoring means through the meniscus and then through the joint capsule to exit through a previously made incision. The suture is then pulled substantially flush with the meniscus across the tear, whereby the surgeon may then pull the needles through the incision, which had been made to expose the outer surface of the joint capsule. The needles are then cut, or may be detached by a sharp pull when the suture contacts the meniscus across the tear. The barbed anchoring means are then cut substantially flush with the joint capsule on the side opposite the suture, the incision is closed; and the anchoring means holds the suture in place The barbs on the anchoring means serve to maintain the position of the device within the meniscus, and the suture and anchoring means serve to maintain the tear at close approximation to enhance healing The material compositions of the suture and the anchoring means are selected to provide the desired resorption rate to allow sufficient time for healing.

In the event that the tissue being repaired is not sufficiently strong to retain the barb members in place, a retaining flange may be utilized which is slipped over the barbs after it is drawn through the tissue to apply counter pressure against the surface of the joint capsule to pull the suture tight across the tear.

BRIEF DESCRIPTION OF THE DRAWINGS

The foregoing features of the present invention will become more readily apparent and may be understood by referring to the following detailed description of an illustrative embodiment of the device for repairing torn tissue and muscle, taken in conjunction with the accompanying drawings, in which:

FIG. 4 illustrates a cut-away perspective view of

FIG. 3 along line 4—4 showing the device of the present invention in position during the meniscal repair procedure;

DETAILED DESCRIPTION OF THE PREFERRED EMBODIMENTS

Figure 1:
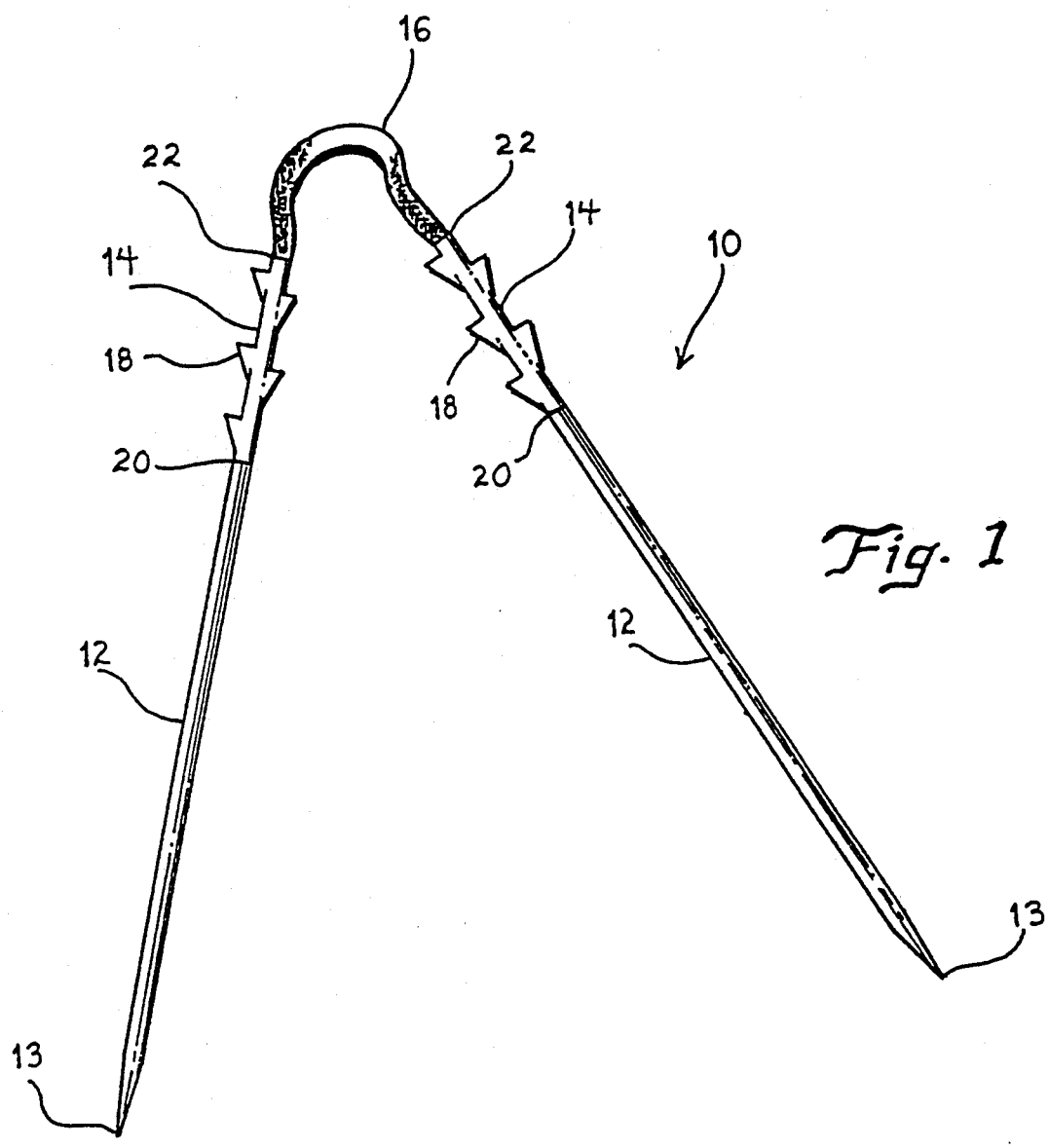
FIG. 1 illustrates a perspective view of the device of the present invention.

Referring now in specific detail to the drawings, in which like reference numerals identify similar or identical elements throughout the several views, FIG. 1 shows the repair device 10 of the present invention. Repair device 10 generally comprises a pair of metal needles 12, preferably constructed of stainless steel or other surgical metal alloy, having a sharp tip 13 at one end to facilitate penetration through tissue, and a blunt end at the other end. In a preferred embodiment, the length of each needle is between 6 inches and 10 inches. However, this is not intended to be limiting as clearly needles of various lengths may be utilized.

Secured to needles 12 are a pair of anchoring members 14 which are constructed of a bioresorbable material, such as homopolymers and copolymers of lactide, glycolide, polydioxanone, trimethylene carbonate, polyethylene oxide or other bioabsorbable materials or blends of these copolymers. Preferably, the anchoring members 14 are formed of a copolymer of lactide and glycolide. Anchor members 14 are linked by a flexible material 16 such as a suture, also constructed of a bioresorbable material, such as a lactide/glycolide copolymer. Flexible material 16 allows for movement of anchoring members 14 with respect to one another. Anchor members 14 preferably have a length of between about 1 inch and 2 inches.

Figure 8:
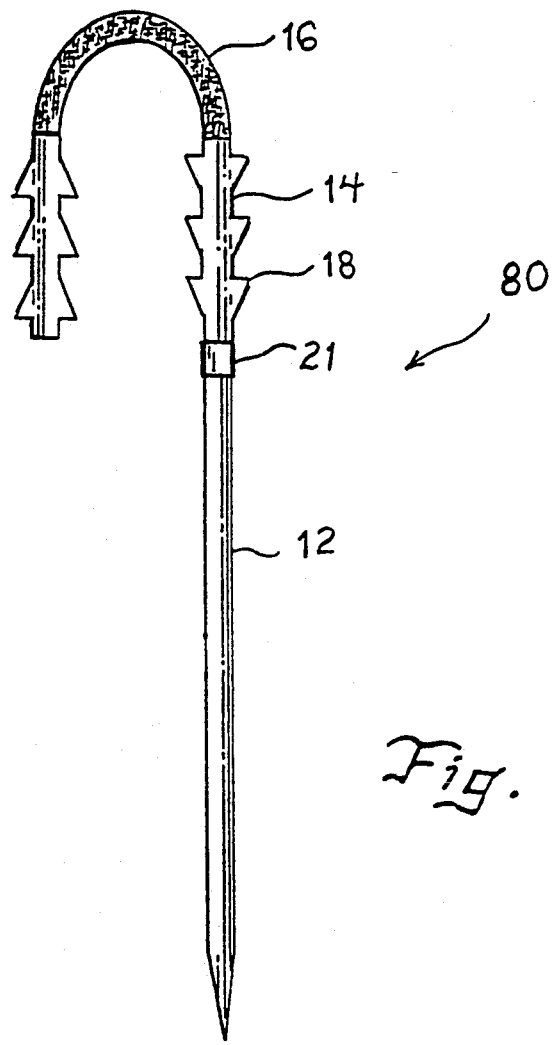
FIG. 8 illustrates a perspective view of another alternate embodiment of the device of FIG. 1.

Needles 12 are secured to anchor members 14 as indicated at joint 20, and the anchor members 14 are secured to suture 16 as at joint 22. The anchor members 14 of device 10 may be secured to the needles 12 by means of adhesives, crimping, swaging or the like, and joint 20 may be formed by heat-shrinkable tubing 21, as seen in FIG. 8. It is preferred that joint 20 is a detachable connection, such that needle 12 may be removed from anchor member 14 by a sharp tug or pull or by cutting as described below. Anchor members 14 are secured to suture 16 preferably by inset molding Anchor members 14 are provided with a plurality of barb-shape projections 18 which serve to anchor device 10 in the tissue to be repaired. Barbs 18 have a tapered shape to allow the anchor members 14 to be pushed through tissue or muscle, such as the menisci of the knee, in a first forward direction and to prevent the anchor members from traveling in a reverse direction. Although as shown in FIG. 1 five barbs 18 are provided, any number may be provided, so long as the barbs penetrate the tissue to anchor the device 10.

Figure 2:
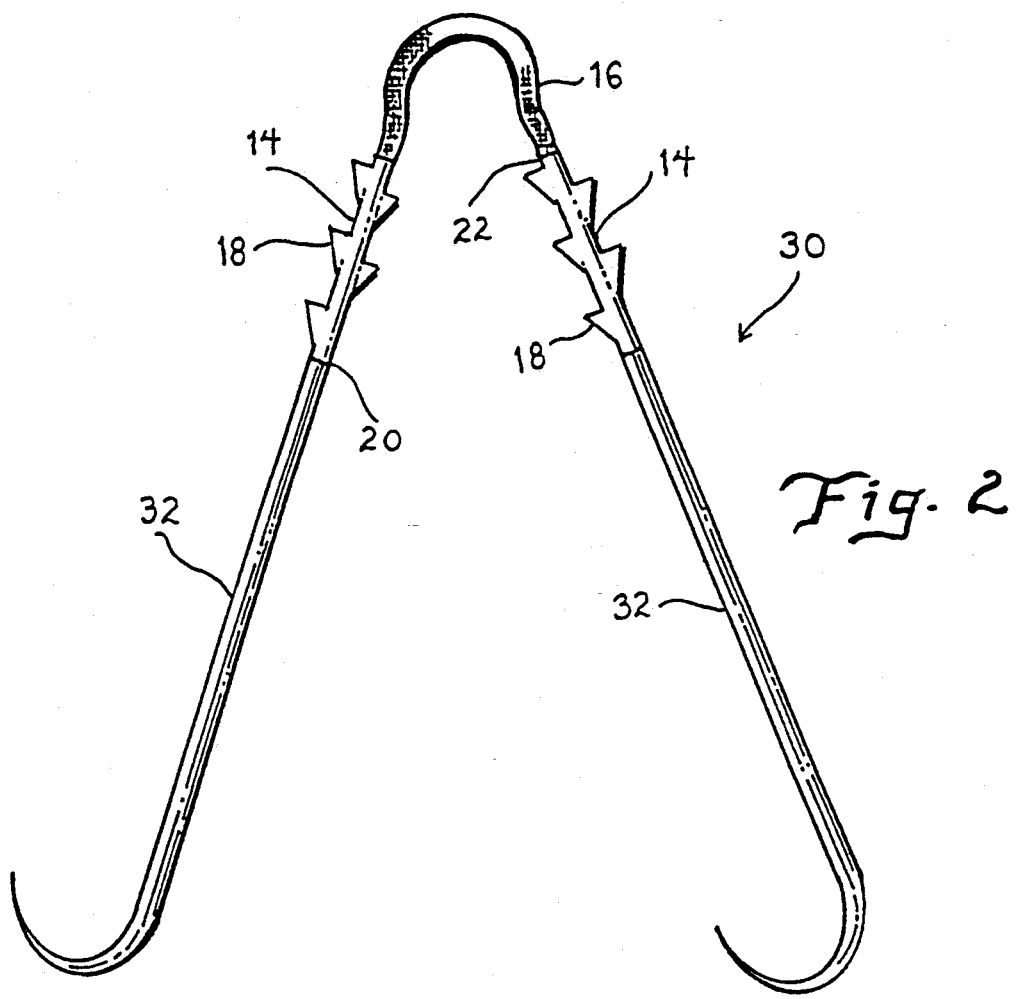
FIG. 2 illustrates a perspective view of an alternate embodiment of the device of the present invention.

FIG. 2 illustrates an alternate embodiment of the device of the FIG. 1. Device 30 is similar in construction to device 10 except that curved needles 32 are provided Needles 32 are secured to anchoring members 14 as described above, which are provided with a plurality of barbs 18 which taper in the direction of needles 32 to facilitate insertion of the device into tissue. Anchor members 14 are connected through suture 16 as described above. The remaining elements of device 30 are identical to those of device 10 as illustrated in FIG. 1.

Figure 3:
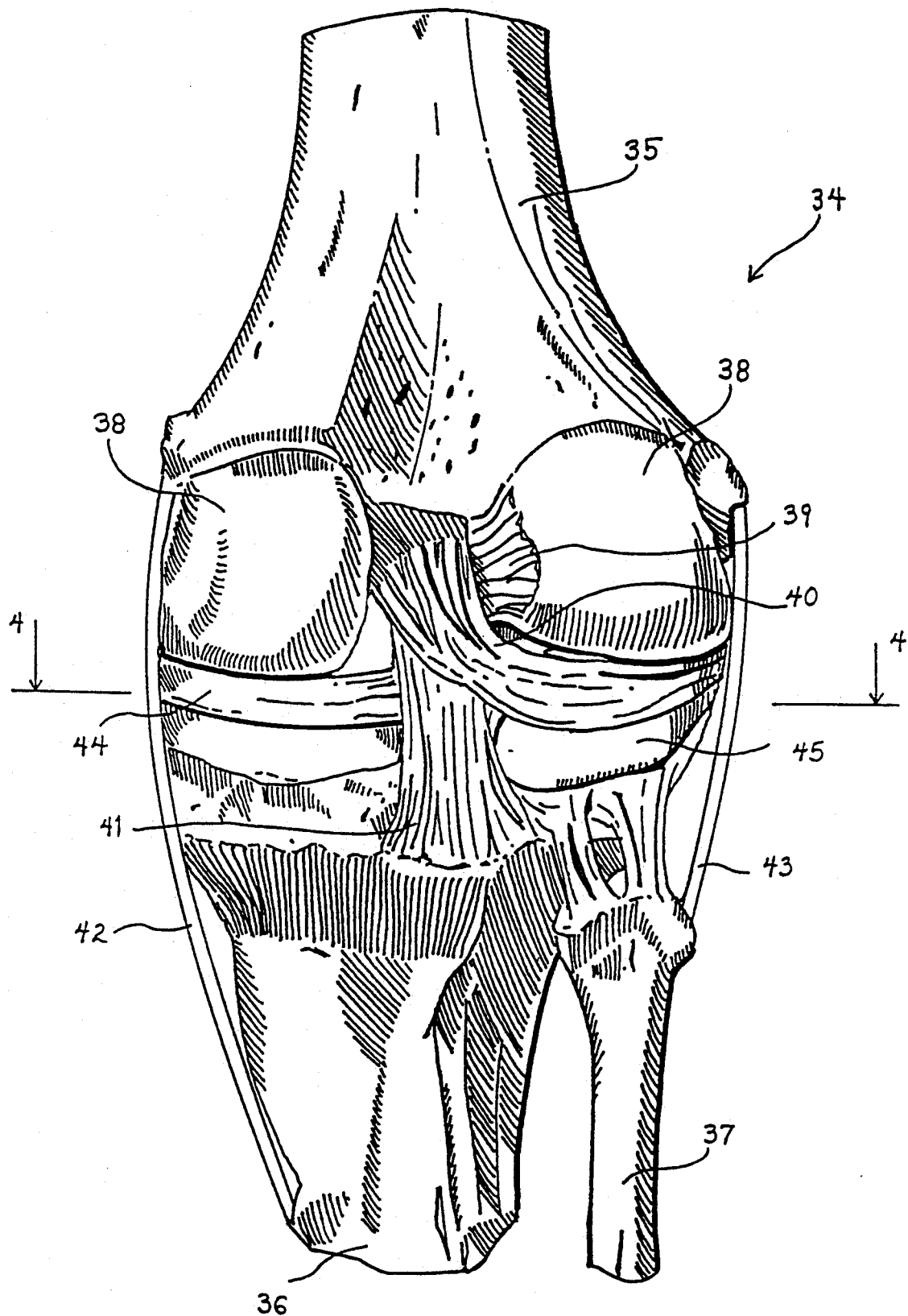
FIG. 3 illustrates a perspective posterior view of the muscular structure of the knee.

FIG. 3 illustrates the muscular and ligament structure of the knee 34, including the pertinent components of the knee to which the present invention is directed. As is well known, the femur 35 is joined to tibia 36 and fibula 37 by muscles, tendons and ligaments, and these bones are separated and cushioned by the medial meniscus 44 and lateral meniscus 45. Condyles 38 of femur 35 rest on the menisci, and the bones are joined and supported by anterior cruciate ligament 39, ligament of Wrisberg 40, posterior cruciate ligament 41, and transverse ligament 46 (see FIG. 5). The joint capsule is formed by tibial collateral ligament 42 and fibular collateral ligament 43.

Figure 4:
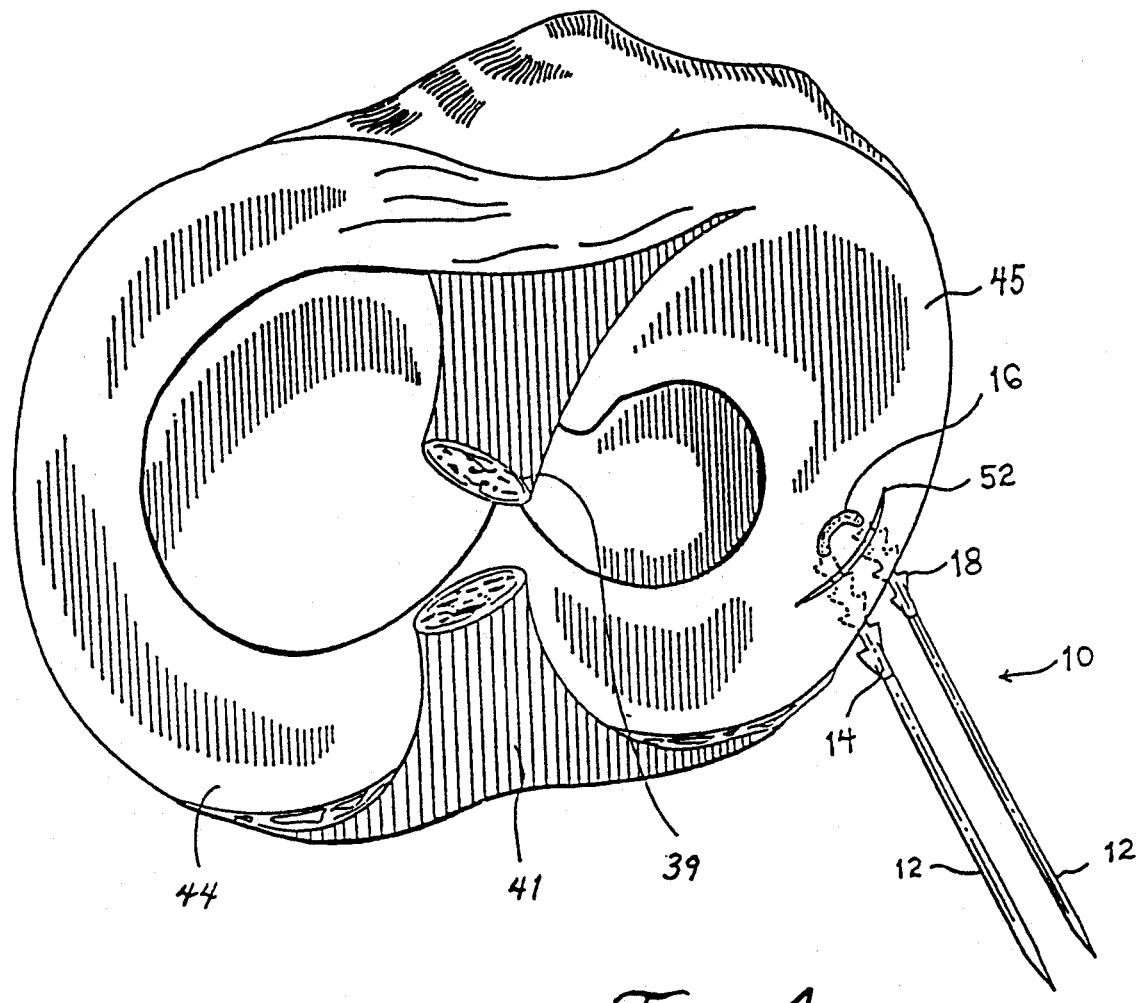

FIG. 4 illustrates the device 10 of the present invention in use, showing knee 34 along lines 4—4 of FIG. 3. The lateral meniscus 45 of a knee 34 having a tear 52 is repaired with the present invention by forcing needles 12 through the meniscus on one side of the tear, through the torn region, and out the meniscus tissue on the opposite side of the tear on the outside of the knee. The device is fully inserted so that flexible member 16 becomes substantially flush with meniscus 45 and is pulled taut. Barbs 18 of anchor members 14 anchor the device in the meniscus 45 and prevent the device from backing off, so that tear 52 is maintained in an abutting relationship across itself to facilitate healing. Needles 12 may then be removed from anchoring members 14 by means of a sharp yank or tug, or are cut as they are accessed from the opposite side of the knee by a suitable incision. Anchoring members 14 are then trimmed so as to be flush with the surface of meniscus 45 or the joint capsule. The material of which anchor members 14 and suture 16 are constructed are preferably bio-resorbable materials which resorb at a rate which is slow enough to facilitate healing of the tear in the tissue.

Figure 5:
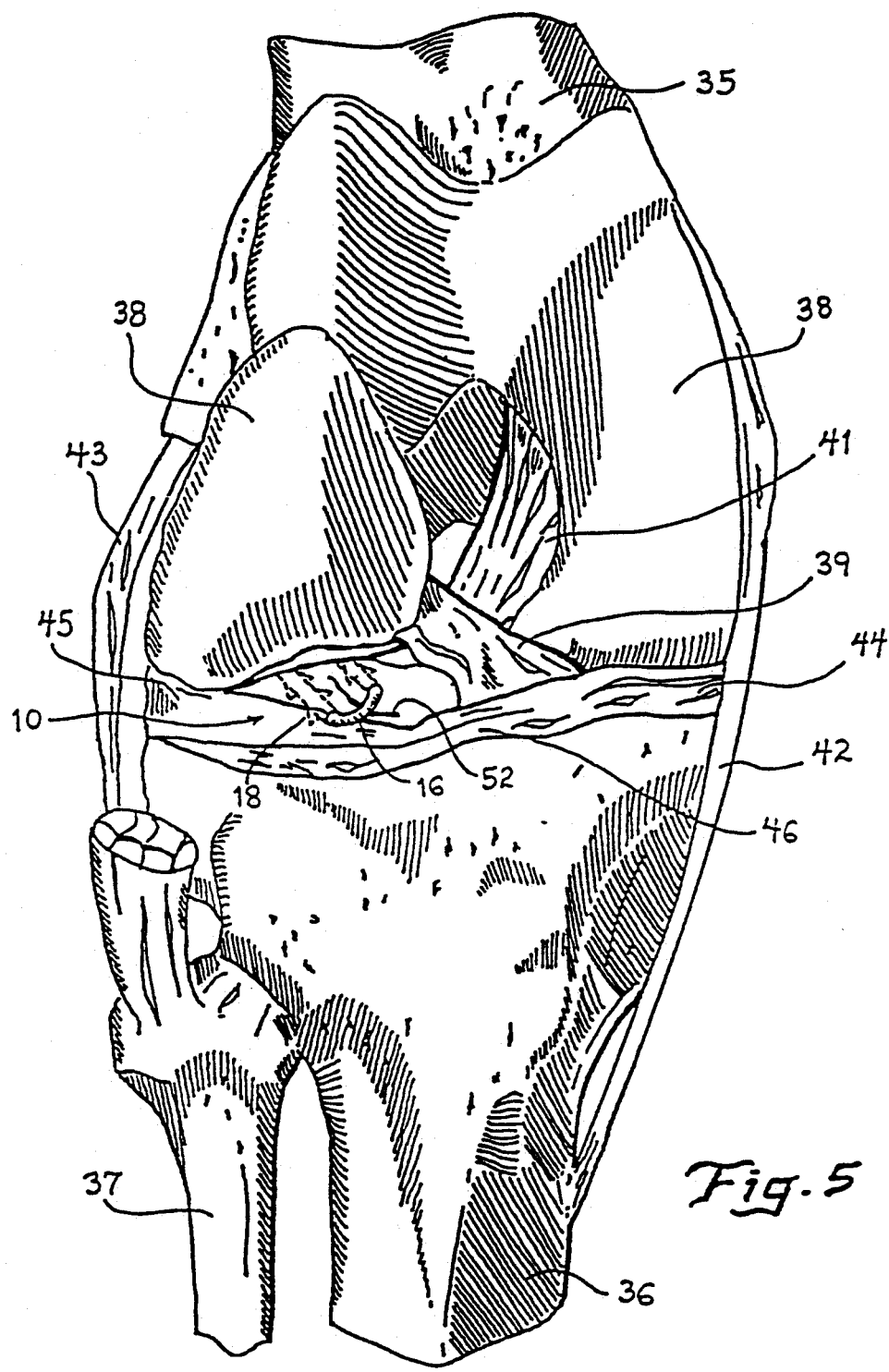
FIG. 5 illustrates a perspective anterior view of the knee of FIG. 3 with the device of the present invention in position during the meniscal repair procedure.

During arthroscopic surgery, as best seen in FIG. 5, the surgeon will approach the torn meniscus from in front of the knee and insert the two needles 12 into the meniscus 44 or 45. As the needles 12 are pushed through the meniscus 45 to draw the edges of the tear together, the surgeon will make an incision on the opposite side of the knee adjacent the needles to avoid pushing the needles through the skin. As the needles are withdrawn, the suture 16 is pulled tight to hold the edges of the tear together while the barbs 18 prevent the backing off of the device 10 through the tissue. The needles are then removed, and the anchor members are trimmed to the surface level of the joint capsule and the incisions are stitched.

Figure 6:
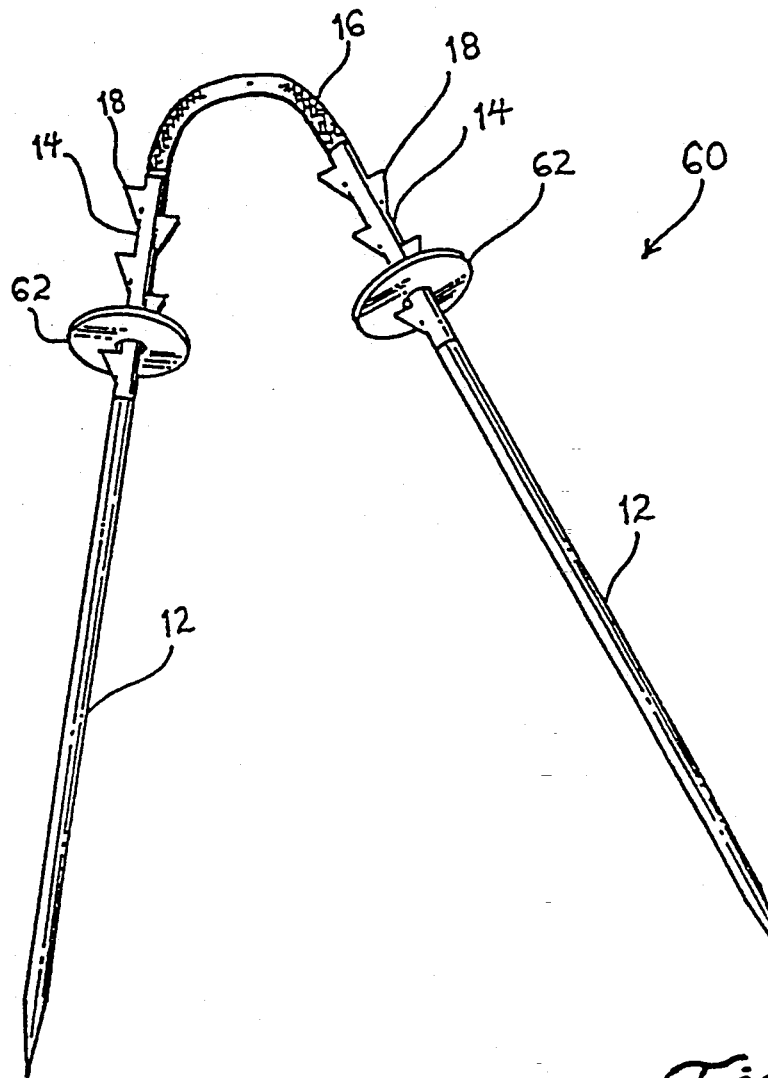
FIG. 6 illustrates a perspective view of an alternate embodiment of the device of FIG. 1.

Turning now to FIG. 6, there is shown a further embodiment of the device of the present invention. Device 60 is identical to device 10 except for the provision of retaining flanges 62 which slip over needles 12 and anchoring members 14 to apply counter pressure against the surface of the joint capsule to pull the suture 16 tight across the tear in the meniscus. Flanges 62 are utilized when the strength of the tissue through which the device passes is insufficient to hold barbs 18 in place.

Figure 7:
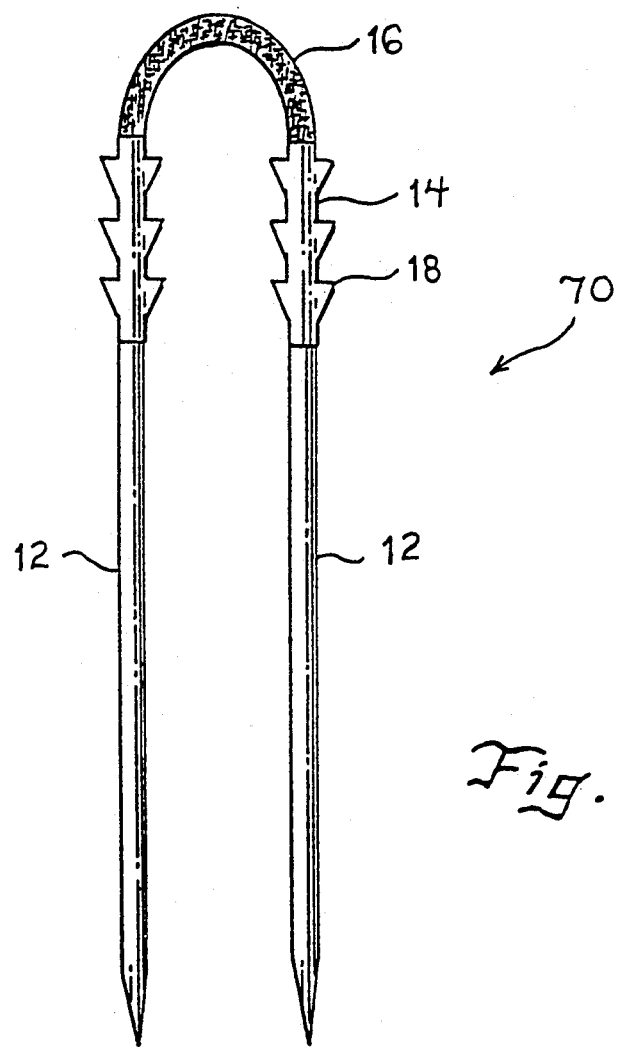
FIG. 7 illustrates a perspective view of a further alternate embodiment of the device of FIG. 1.

FIG. 7 illustrates a further embodiment of the device of the present invention. Device 70 is identical to device 10 except that barbs 18 are aligned with each other, rather than staggered as in accordance with FIG. 1 Clearly, device 70 may include curved needles as shown in FIG. 2 or retaining flanges 62 as shown in FIG. 6.

While the invention has been particularly shown and described with reference to the preferred embodiments, it will be understood by those skilled in the art that various modifications and changes in form and detail may be made therein without departing from the scope and spirit of the invention. Accordingly, modifications such as those suggested above, but not limited thereto, are to be considered within the scope of the invention.

The device may have another embodiment which is a surgical needle is detachably secured at a first end to a first anchoring member. A suture member is secured to a first end of the anchoring member and a second anchoring member is secured to a second end of the suture as seen in FIG. 8.

What is claimed is:

1. A tissue tear repair device comprising:
   a pair of tissue piercing members; and
   a pair of tissue connecting members having first and second ends, said tissue connecting members being joined to each other at respective first ends by flexible material extending therebetween, said tissue connecting members being constructed of a material having a greater rigidity than said flexible material to facilitate retention of said tissue connecting members in said tissue;
   wherein said tissue piercing members comprise a pair of straight surgical needles, each of said needles being detachably secured at respective second ends to a respective one of said tissue connecting members, each of said needles being detachable from said tissue connecting member by pulling or cutting.

2. A tissue tear repair device according to claim 1, further comprising at least one retaining flange member which fits over said tissue piercing members and said tissue connecting members.

3. A tissue tear repair device according to claim 1, wherein said tissue connecting members comprise resorbable material.

4. A tissue tear repair device according to claim 1, wherein said anchoring means of said tissue connecting members comprises a plurality of barb-shape members which hold the tissue connecting members in place across a tear in tissue.

5. A tissue tear repair device according to claim 4, wherein said barb-shape members have a tapered shape towards said second ends of said tissue connecting members to permit penetration through tissue in a forward direction but prevent movement in a reverse direction.

6. A tissue tear repair device according to claim 1 wherein said tissue connecting members are secured to said tissue piercing members by one of adhesives, swaging, and crimping.

7. A tissue tear repair device according to claim 1, wherein said tissue connecting members are secured to said tissue piercing members by heat shrinkable tubing.

8. A device according to claim 1, wherein said flexible material comprises a resorbable suture.

9. A tissue tear repair device according to claim 1, wherein said tissue connecting members include anchoring means for securing said tissue connecting members in said tissue.

10. A tissue tear repair device comprising:
    a pair of tissue piercing members; and
    a pair of tissue connecting members having first and second ends, said tissue connecting members being joined to each other at respective first ends by flexible material extending therebetween, said tissue connecting members being constructed of a material having a greater rigidity than said flexible material to facilitate retention of said tissue connecting members in said tissue;
    wherein said tissue piercing members comprise a pair of curved surgical needles, each of said needles being detachably secured at respective second ends to a respective one of said tissue connecting members, each of said needles being detachable from said tissue connecting member by pulling or cutting.

11. A device for repairing torn tissue, in particular the meniscus of the knee, comprising:
    a pair of tissue piercing members each having a pointed end and a blunt end;
    a pair of tissue anchoring members being secured at a first end to said piercing members at said blunt ends; and
    a linking member for joining said anchoring members together, said linking member joining an end of each anchoring member at a second end,
    wherein said anchoring members are constructed of a material of greater rigidity than said linking member to facilitate retention of said anchoring members is said torn tissue and wherein said tissue piercing members comprise surgical needles detachably secured to said tissue anchoring members 12. A device according to claim 11, wherein said linking member comprises a suture.

13. A device according to claim 12, wherein said anchoring members are composed of resorbable material.

14. A device according to claim 11, wherein each of said tissue piercing members comprises a straight metal needle.

15. A device according to claim 11, wherein said tissue anchoring members include a plurality of barb-shape projections extending outwardly from said tissue anchoring members.

16. A device for repairing torn meniscal tissue comprising
    a pair of surgical needles,
    a pair of tissue anchoring members detachably secured at a first end to each needle, and
    a suture secured to each anchoring member at a second end to join said anchoring members together,
    wherein said anchoring members are constructed of a material of greater rigidity than said suture to facilitate retention of said anchoring members in said torn meniscal tissue.

17. A device according to claim 16, wherein said tissue anchoring member and said suture are constructed of resorbable material.

18. A device according to claim 16, wherein said anchoring members include a plurality of barb-shape projections for grasping tissue.

19. A device for repairing torn meniscal tissue comprising a surgical needle, a first anchoring member detachably secured at a first end to said surgical needle, a suture member secured at a first end to a second end of said first anchoring members, and a second anchoring member secured to a second end of said suture member, wherein said anchoring members are constructed of a material of greater rigidity than said suture member to facilitate retention of said anchoring members in said torn meniscal tissue said surgical needle being detachable from said first anchoring member by pulling or cutting.

20. A device according to claim 19, wherein said first and second anchoring members are provided with a plurality of outwardly projecting barbs for grasping tissue.

* * * * *